(12) United States Patent
Jeong

(10) Patent No.: US 11,490,847 B2
(45) Date of Patent: Nov. 8, 2022

(54) ELECTRONIC DEVICE FOR DETECTING BIOMETRIC INFORMATION

(71) Applicant: Samsung Electronics Co., Ltd., Gyeonggi-do (KR)

(72) Inventor: Injo Jeong, Gyeonggi-do (KR)

(73) Assignee: Samsung Electronics Co., Ltd.

( * ) Notice: Subject to any disclaimer, the term of this patent is extended or adjusted under 35 U.S.C. 154(b) by 769 days.

(21) Appl. No.: 16/399,233

(22) Filed: Apr. 30, 2019

(65) Prior Publication Data
US 2019/0328264 A1   Oct. 31, 2019

(30) Foreign Application Priority Data
Apr. 30, 2018   (KR) .................. 10-2018-0049678

(51) Int. Cl.
*A61B 5/257* (2021.01)
*A61B 5/259* (2021.01)
*A61B 5/291* (2021.01)

(52) U.S. Cl.
CPC .............. *A61B 5/259* (2021.01); *A61B 5/291* (2021.01); *A61B 2562/0209* (2013.01)

(58) Field of Classification Search
CPC .......... A61B 5/24; A61B 5/259; A61B 5/291; A61B 2562/0209; A61B 5/257; A61B 5/25
See application file for complete search history.

(56) References Cited

U.S. PATENT DOCUMENTS

| 4,051,842 A | 10/1977 | Hazel et al. | |
|---|---|---|---|
| 9,220,431 B2 * | 12/2015 | Holzhacker | .......... A61B 5/0536 |
| 2003/0149349 A1 | 8/2003 | Jensen | |
| 2006/0150714 A1 * | 7/2006 | Imhof | ................... A61B 5/4266 73/29.01 |
| 2006/0182788 A1 * | 8/2006 | Singh | .................... A61N 1/0456 424/448 |
| 2006/0224072 A1 * | 10/2006 | Shennib | ............... A61B 5/6833 600/509 |

(Continued)

FOREIGN PATENT DOCUMENTS

| JP | 2017-023754 | 2/2017 |
|---|---|---|
| KR | 1020150108580 | 9/2015 |

(Continued)

OTHER PUBLICATIONS

Translation of KR-101819679-B1, Oh Guen Young, KR, Jan. 2018 (Year: 2018).*

(Continued)

*Primary Examiner* — Eun Hwa Kim
*Assistant Examiner* — Adam Z Minchella
(74) *Attorney, Agent, or Firm* — The Farrell Law Firm, P.C.

(57) ABSTRACT

An electronic device is provided. The electronic device includes a housing including at least one electronic component, and a pad structure coupled with the housing, and attached to a user body. The pad structure includes a first adhesive material having an adhesive strength at which the electronic device holds attachment in response to lack of existing water or humidity, and a second adhesive material abutting the first adhesive material and having an adhesive strength at which the electronic device holds the attachment in response to existing water or humidity.

19 Claims, 12 Drawing Sheets

(56) References Cited

U.S. PATENT DOCUMENTS

| | | | |
|---|---|---|---|
| 2006/0269472 A1* | 11/2006 | Mackinnon | C01B 39/48 423/709 |
| 2007/0032719 A1* | 2/2007 | Menon | C09J 9/02 252/500 |
| 2008/0275327 A1* | 11/2008 | Faarbaek | A61B 5/68335 600/382 |
| 2014/0062654 A1* | 3/2014 | Cok | G06K 19/0717 340/5.61 |
| 2014/0206976 A1* | 7/2014 | Thompson | G16Z 99/00 600/391 |
| 2015/0082623 A1 | 3/2015 | Felix et al. | |
| 2015/0335288 A1* | 11/2015 | Toth | A61B 5/6833 600/391 |
| 2016/0026297 A1 | 1/2016 | Shinkai et al. | |
| 2016/0174885 A1 | 6/2016 | Hahn et al. | |
| 2016/0242654 A1* | 8/2016 | Quinlan | A61B 5/259 |
| 2018/0000347 A1* | 1/2018 | Perez | A61N 1/36014 |
| 2018/0132791 A1* | 5/2018 | Chen | A61B 5/282 |

FOREIGN PATENT DOCUMENTS

| | | | | |
|---|---|---|---|---|
| KR | 1020170027646 | 3/2017 | | |
| KR | 10-1819679 | 1/2018 | | |
| KR | 101819679 B1 * | 1/2018 | | A61B 6/145 |
| WO | WO 2006/094513 | 9/2006 | | |
| WO | WO 2011/143490 | 11/2011 | | |

OTHER PUBLICATIONS

European Search Report dated Mar. 1, 2021 issued in counterpart application No. 19796898.5-1113, 8 pages.

International Search Report dated Aug. 2, 2019 issued in counterpart application No. PCT/KR2019/004978, 7 pages.

* cited by examiner

ELECTRONIC DEVICE FOR DETECTING BIOMETRIC INFORMATION

CROSS-REFERENCE TO RELATED APPLICATION(S)

This application is based on and claims priority under 35 U.S.C. § 119 to Korean Patent Application Serial No. 10-2018-0049678, filed on Apr. 30, 2018 in the Korean Intellectual Property Office, the entire disclosure of which is incorporated herein by reference.

BACKGROUND

1. Field

The present disclosure relates generally to an electronic device capable of being attached to part of the user's body for obtaining biometric information.

2. Description of Related Art

The smart health care market is coming into blossom in engagement with an increased interest in health, entering into the aging society, and a fusion of an information telecommunication technology and the medical industry. For example, numerous health care devices or related applications for specialized and systematic collection and/or analysis of personal medical information are now available. The health care devices can interwork with smart phones and add a social networking factor to provide a new user experience (UX) to users, and can gather and analyze health related data to provide integrated health care to the users.

The above information is presented as background information only to assist with an understanding of the present disclosure. No determination has been made, and no assertion is made, as to whether any of the above might be applicable as prior art with regard to the present disclosure.

SUMMARY

To continuously detect a user's biometric information, the health care device can have a form of a watch being worn on the wrist, or have a form of a patch being directly attached to the user's skin. For heart disease measurement, there is a need to measure conditions in which arrhythmia, stricture of the heart, myocardial infarction, etc. are generated for a long time (e.g., 24 hours or more), to synthetically determine a state of the heart. To be attached to the user's body (e.g., the chest portion) long time, the health care device of the patch form may need an adhesion force for guaranteeing a durability (or continuity) of attachment. The health care device may need a re-adhesion force to make repeated use possible. The health care device may need to compensate for conditions such as inconvenience of direct attachment to the user's skin, attachment and detachment pain, and/or skin troubles. Further, the health care device may need to prevent adhesion force deterioration caused by moisture (e.g., sweat) generated from the user's skin.

The present disclosure has been made to address at least the disadvantages described above and to provide at least the advantages described below.

In accordance with an aspect of the present disclosure, an electronic device is provided. The electronic device includes a housing including a first housing surface facing a first direction, at least one electronic component positioned within the housing, at least one electrode exposed through the first housing surface and electrically coupled with the electronic component, and a pad structure coupled with the housing. The pad structure includes a first adhesive layer which includes a first adhesive surface attached to at least a part of the first housing surface and a second adhesive surface of an opposite direction to the first adhesive surface, a second adhesive layer which includes a third adhesive surface facing the second adhesive surface, and a fourth adhesive surface of an opposite direction to the third adhesive surface. The second adhesive layer includes at least one first region which includes a first adhesive material having a first adhesive strength in response to water or humidity existing and having a second adhesive strength greater than the first adhesive strength in response to the water or humidity not existing, and at least one second region which abuts the first region and includes a second adhesive material having a third adhesive strength in response to the water or humidity not existing, and having a fourth adhesive strength greater than the third adhesive strength in response to the water or humidity existing. The pad structure includes a substrate layer in contact with the first adhesive layer and the second adhesive layer, and positioned therebetween, at least one opening formed through at least a part of the pad structure, and an electrolyte in contact with the at least one electrode and filling at least part of the opening.

In accordance with an aspect of the present disclosure, an electronic device is provided. The electronic device includes a housing including at least one electronic component, and a pad structure coupled with the housing, and attached to a user's body. The pad structure includes a first adhesive material having an adhesive strength at which the electronic device holds attachment in response to water or humidity not existing, and a second adhesive material abutting the first adhesive material and having an adhesive strength at which the electronic device holds the attachment in response to the water or humidity existing.

BRIEF DESCRIPTION OF THE DRAWINGS

The above and other aspects, features and advantages of certain embodiments of the disclosure will be more apparent from the following detailed description taken in conjunction with the accompanying drawings, in which.

DETAILED DESCRIPTION

Figure 1:
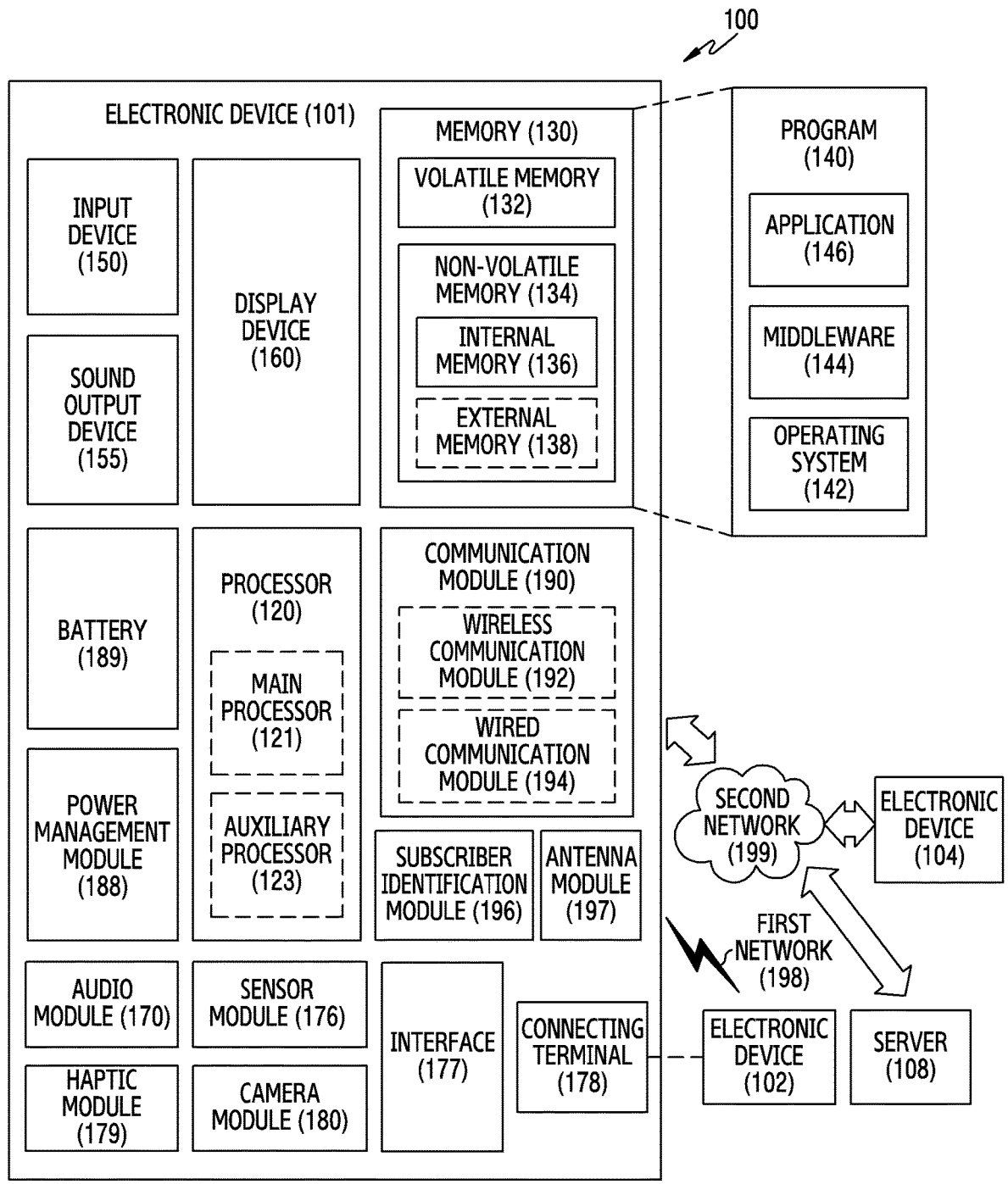
FIG. 1 is a block diagram of an electronic device within a network environment, according to an embodiment.

Various embodiments are described below in detail with reference to the accompanying drawings. However, for description convenience's sake, the sizes of components in the drawings may be exaggerated or reduced. For instance, for description convenience's sake, a size and thickness of each component shown in the drawings are arbitrarily shown and therefore, the disclosure is not necessarily limited to the illustrated drawings. Also, a rectangular coordinate system is used, wherein a direction of an x axis may refer to a horizontal direction of an electronic device, and a y axis may refer to a vertical direction of the electronic device, and a z axis may refer to a thickness direction of the electronic device. However, the x axis, the y axis and the z axis may be construed as a wide meaning which includes, but are not limited to, three axes on the rectangular coordinate system. For example, the x axis, the y axis and the z axis may mutually meet at right angles, or may denote mutually different directions not meeting at right angles. In relation to a description of the drawing, like reference symbols may be used for like components.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
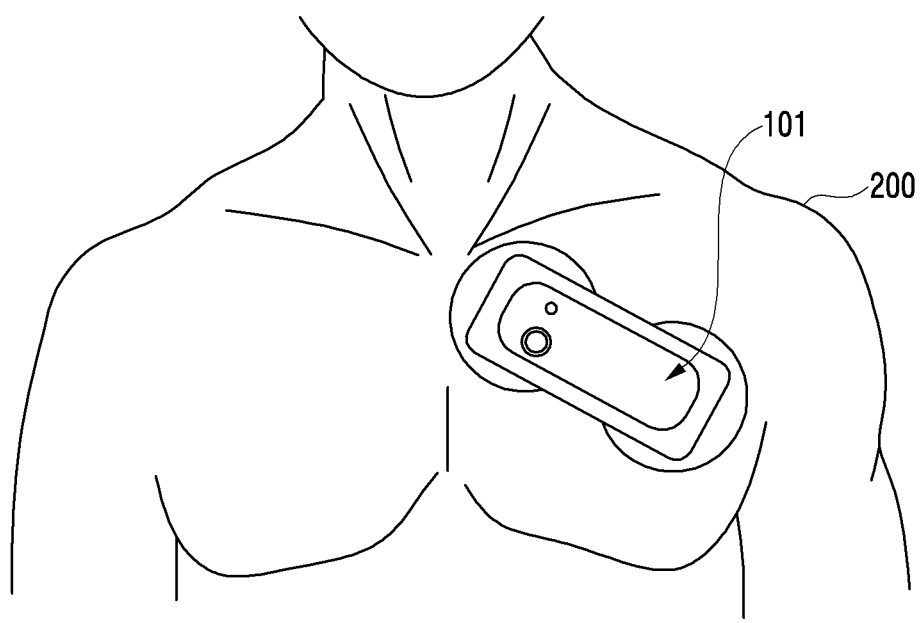
FIG. 2 is a diagram of a state in which an electronic device is attached to the user's body, according to an embodiment.

FIG. 2 is a diagram of a state in which the electronic device 101 is attached to the user's body 200, according to an embodiment. The electronic device 101 may be a portable health care device (or a biometric information obtaining device) capable of being attached to the user's body 200 (for example, the chest). This is merely an example, and the electronic device 101 may be electronic devices of various forms in which long-time attachment to the user's body 200 is required.

For user's heart disease measurement, the electronic device 101 may be attached to part of the user's chest, to measure electrocardiogram (ECG). The electronic device 101 may measure the electrocardiogram through a change of an electric signal dependent on the movement of the heart. The electrocardiogram is a graph record of measurement of a potential difference of an action current provided in response to the heart being contracted and relaxed and spreading from the heart to the whole body, the potential difference being provided between any two points of the chest. Generally, it is difficult to obtain heart diseases such as arrhythmia, stricture of the heart, myocardial infarction, etc., through short-time measurement and thus, long-time measurement is required. The above description is made in which the electronic device 101 includes an electrocardiogram sensor for measuring electrocardiogram. However, the electronic device 101 may include various sensors (e.g., a lactic acid sensor) capable of obtaining (or measuring) information from the human skin or saliva (e.g., tear, sweat, etc.).

The electronic device 101 may be needed to be attached to the user's body 200 for a long time (e.g., 24 hours or more), where the electronic device 101 predicts heart diseases such as arrhythmia, stricture of the heart, myocardial infarction, etc. The electronic device 101 may be stably attached to the user's body 200 for three days or more.

Figure 3A:
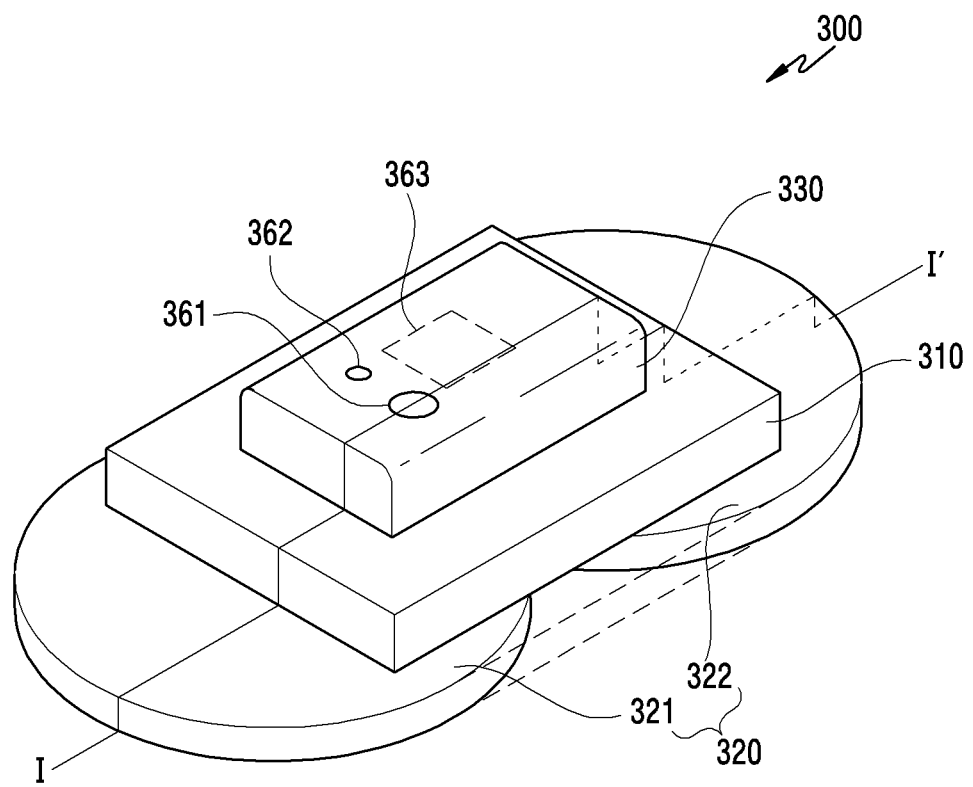
FIG. 3A is a diagram of an electronic device, according to an embodiment.
Figure 3B:
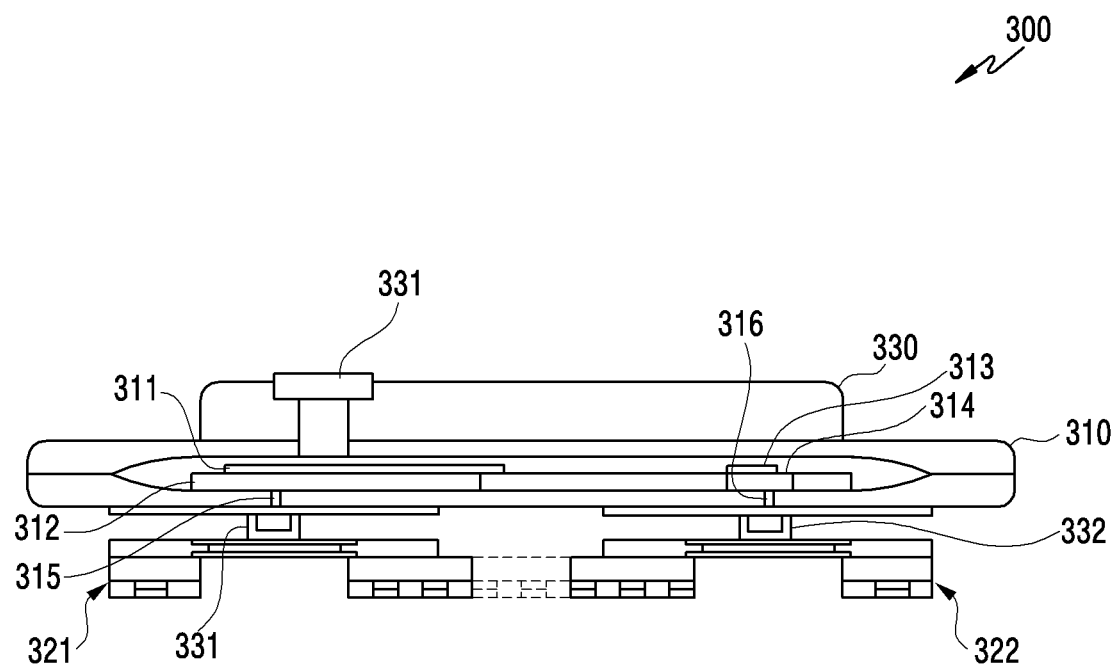
FIG. 3B is a diagram of a section taken along line I-I' of the electronic device of FIG. 3A, according to an embodiment.
Figure 3C:
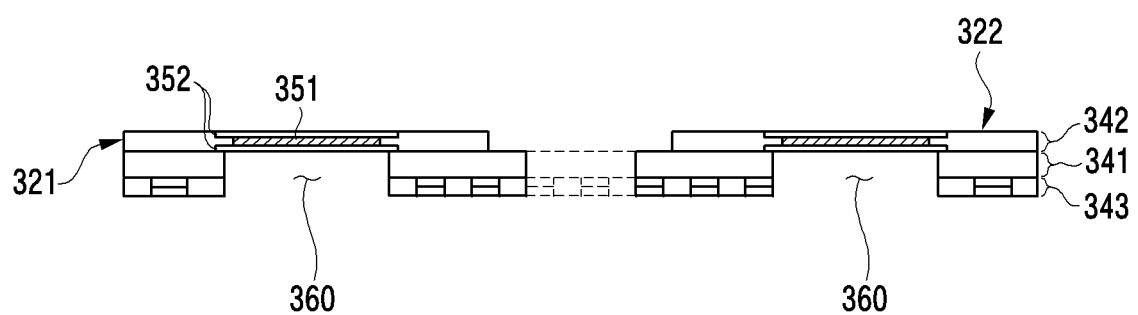
FIG. 3C is a diagram of a cross section of a pad structure of the electronic device of FIG. 3B, according to an embodiment.

FIG. 3A is a diagram of an electronic device 300, according to an embodiment. FIG. 3B is a diagram of a section taken along line I-I' of the electronic device of FIG. 3A, according to an embodiment. FIG. 3C is a diagram of a cross section of a pad structure of the electronic device of FIG. 3B, according to an embodiment. The electronic device 300 illustrated in FIG. 3A to FIG. 3C may be an electronic device having the same or at least partly similar construction with the electronic device 101 of FIG. 1 and FIG. 2.

Referring to FIG. 3A, the electronic device 300 may include a housing 310, a pad structure 320, and a cover 330.

The housing 310 may include a first housing surface facing a first direction (i.e., a lower end direction), include various electronic components therein, and include at least one electrode 315 and 316 exposed through the first housing surface and electrically coupled with the electronic components. The electronic component may include an electronic circuit for providing data about an ECG.

The pad structure (or pad structures) 320 may be coupled with the housing 310, and be attached to the user's body (e.g., the body 200 of FIG. 2). A coupling structure of the pad structure 320 and the housing 310 is described later with reference to FIG. 10.

The cover 330 may be disposed on the housing 310. At least one of a button 361, an indicator 362, and a display 363 may be disposed on the cover 330.

The housing 310 may be coupled to the pad structure 320, and be attached to the user's body by means of an adhesion force of the pad structure 320. The pad structure 320 may include a first pad 321 and a second pad 322. The number of pads included in the pad structure 320 may be variable according to a measurement item of the electronic device 300. In response to measuring only either electrocardiogram or fatigue (blood glucose), the pad structure 320 may include two pads and, in response to measuring both the electrocardiogram and the fatigue, the pad structure 320 may include four pads (each includes two). The pad structure 320 may include three pads including one pad which is commonly used for the electrocardiogram measurement and the fatigue measurement.

Referring to FIG. 3B, the electronic device 300 may include a plurality of electrodes for obtaining user's biometric information. The electronic device 300 may include a first electrode 331 and a second electrode 332. The electronic device 300 may be configured to measure an ECG by using respective current values measured by the first electrode 331 and the second electrode 332. The electronic device 300 may include various electronic components for driving of the first electrode 331 and the second electrode 332 (e.g., a power source for voltage applying, an amplifier, and a plurality of filter portions for current value measurement). The electronic device 300 may include at least one processor 311 for controlling the above-mentioned various electronic components and electrodes 331 and 332. The electronic device 300 may include a printed circuit board 312 within the housing 310. The at least one processor 311 and/or other electronic components may be mounted on the printed circuit board 312. A communication module 313 (e.g., the communication module 190) enabling the electronic device 300 to communicate with other electronic devices and/or an actuator 314 may be further mounted in the printed circuit board 312.

The first electrode 331 may be coupled to the first pad 321, and the second electrode 332 may be coupled to the second pad 322. The first electrode 331 and the second electrode 332 may be closely attached to the user's body through the pad structure 320, to obtain a change of an electric signal dependent on the movement of the heart.

Referring to FIG. 3C, the first pad 321 and the second pad 322 may each include a pad upper end portion 342 and an adhesive portion 343 that are each laminated up and down with a criterion of an adhesive fixing film portion 341. The adhesive fixing film portion 341 may be a substrate layer, which gets in contact with the pad upper end portion 342 and the adhesive portion 343 and is positioned therebetween.

The pad upper end portion 342 may be a first adhesive layer, which includes a first adhesive surface attached to at least part of the first housing surface of the housing 310 and a second adhesive surface of an opposite direction to the first adhesive surface. The pad upper end portion 342 may include an electrolyte preservation portion 352. The electrolyte preservation portion 352 may be electrically coupled to an electrode (e.g., the first electrode 331 and the second electrode 332) and may be filled with an electrolyte 351.

The electrolyte 351 may be comprised of water, tartaric acid, glycerin, sodium polyacrylate, and polyethylene glycol. The electrolyte 351 may be comprised of about 30 to 70 weight % of water, about 0.5 to 5 weight % of tartaric acid, about 20 to 50 weight % of glycerin, about 5 to 10 weight % of sodium polyacrylate, and about 1 to 6 weight % of polyethylene glycol. The water included in the electrolyte 351 may contribute to an electric conductivity, and hydrate and soften a horny layer of the skin, to promote the percutaneous absorption of the electrolyte 351. The tartaric acid included in the electrolyte 351 may adjust pH of the electrolyte 351, and hold a stability of the electrolyte 351 and a percutaneous absorption state of the electrolyte 351. The glycerin included in the electrolyte 351 may maintain moisture retention. The sodium polyacrylate included in the electrolyte 351 may improve a sustainability and stability of moisture content, and enhance percutaneous adhesiveness. Also, the sodium polyacrylate included in the electrolyte 351 may prevent stickiness or laxation, and may ease a pain at peeling off from the skin and prevent an electrolyte element from remaining in the skin. The polyethylene glycol may uniformly dissolve or disperse the electrolyte element in a dissolution dispersive form, to stably hold and discharge the electrolyte element within the electrolyte, and promote the percutaneous absorption. The polyethylene glycol included in the electrolyte 351 may prevent conductive materials within the electrolyte 351 from being precipitated as a crystal, to promote the percutaneous absorption.

The electrolyte 351 may include an ion having a high ion conductivity. For example, the electrolyte 351 may include a chloride ion, a sodium ion, a potassium ion, etc. The electrolyte 351 may easily shift a bio-electric signal to the contacted at least one electrode through the movement of the ion.

The pad structure 320 may include at least one opening 360 which is formed in at least part of the pad structure 320. The opening 360 may be surrounded by the adhesive fixing film portion 341 and the adhesive portion 343, and may be formed below the electrolyte preservation portion 352. At least part of the opening 360 may be filled with the electrolyte 351.

The electrolyte preservation portion 352 coupled with the electrodes may be exposed to the external through the opening 360 wherein the electrolyte preservation portion 352 may substantially get in contact with the skin.

The adhesive portion 343 may provide an adhesion force capable of attaching the electronic device 300 to the user's body.

The adhesive portion 343 may be a second adhesive layer, which includes a third adhesive surface facing the second adhesive surface of the pad upper end portion 342 (i.e., the first adhesive layer), and a fourth adhesive surface of an opposite direction to the third adhesive surface.

The adhesive portion 343 may provide an adhesion force capable of stably attaching the electronic device 300 to the user's body for a long time (e.g., three days or more). An adhesive strength of the adhesive portion 343 may be approximately 1.0 N/cm2 or more. Also, the adhesive portion 343 may maintain the adhesion force even upon re-attachment after detachment. Also, even in various conditions (e.g., in response to there being humidity, in response to there being no humidity, etc.), the adhesive portion 343 may provide the adhesion force capable of stably attaching the electronic device 300 to the user's body.

The pad structure 320 may further include a sheet which is attached to the fourth adhesive surface of the adhesive portion 343. The sheet may include polyethylene terephthalate (PET).

Figure 4:
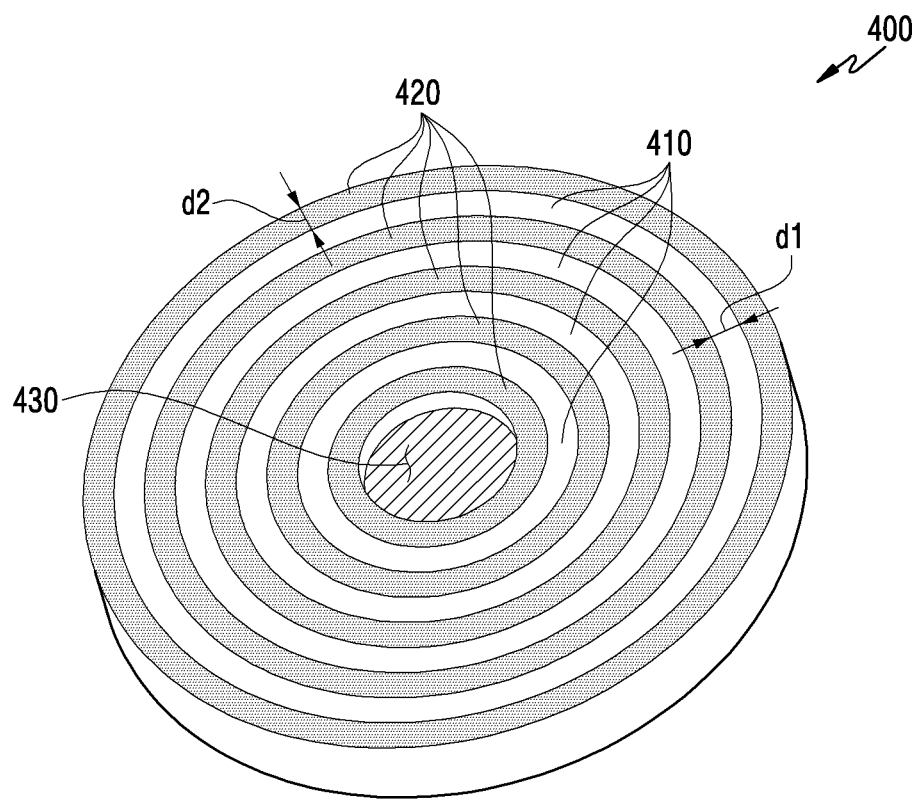
FIG. 4 is a diagram of an adhesive portion, according to an embodiment.

FIG. 4 is a diagram of an adhesive portion 400, according to an embodiment. The adhesive portion 400 explained in FIG. 4 may be a construction which is at least partially similar or the same as the adhesive portion 343 of FIG. 3C.

Referring to FIG. 4, the adhesive portion 400 may include a dry adhesive agent 410 and a wet adhesive agent 420. The dry adhesive agent 410 may have an adhesion force in a dry environment (or an environment of no moisture). The dry adhesive agent 410 may have a first adhesive strength in response to water or humidity existing, and have a second adhesive strength greater than the first adhesive strength in response to the water or humidity not existing. The wet adhesive agent 420 may have an adhesion force in an environment of moisture. The wet adhesive agent 420 may have a third adhesive strength in response to the water or humidity not existing, and have a fourth adhesive strength greater than the third adhesive strength in response to the water or humidity existing. Here, the first adhesive strength and the third adhesive strength may be adhesive strengths of a degree difficult to hold the attachment of the electronic device, and the second adhesive strength and the fourth adhesive strength may be adhesive strengths of a degree being enough to hold the attachment of the electronic device.

The adhesive portion 400 may provide an adhesion force that uses the dry adhesive agent 410 in normal times (e.g., an environment of no moisture), and provide an adhesion force that uses the wet adhesive agent 420 in an environment of moisture. In the environment of moisture (e.g., water or humidity), the attachment of the electronic device may be held by means of the dry adhesive agent 410 having the adhesion force of the first adhesive strength and the wet adhesive agent 420 having the adhesion force of the fourth adhesive strength. On the contrary, in the environment of no moisture (e.g., water or humidity), the attachment of the electronic device may be held by the dry adhesive agent 410 having the adhesion force of the second adhesive strength and the wet adhesive agent 420 having the adhesion force of the third adhesive strength.

The adhesive portion 400 may alternately dispose the dry adhesive agent 410 and the wet adhesive agent 420. A ratio of the dry adhesive agent 410 to the wet adhesive agent 420 may be 7 to 3. However, the disclosure is not limited to this, and may be variable according to a skin condition and area. In response to a climate condition being wet and sweat being a lot, a ratio of the wet adhesive agent 420 may be relatively increased. Even the contrary is possible. The ratio may be different according to the adhesive strengths configuring the dry adhesive agent 410 and the wet adhesive agent 420.

The existing adhesive agent generally used to attach the electronic device to the user's skin includes only the dry adhesive agent. The general dry adhesive agent, an acrylic-based or rubber-based adhesive agent, may be vulnerable to moisture. The acrylic-based and rubber-based adhesive agents have high surface energy and high polarities and therefore, have high reactivity with moisture being polar materials. This may cause a sudden deterioration of an adhesion force. That is, in response to being exposed to a wet environment, the existing adhesive agent may fail to hold the adhesion force.

Compared to the existing adhesive portion including only the dry adhesive agent, the adhesive portion 400 may further include the wet adhesive agent 420 as well as the dry adhesive agent 410, to guarantee a durability of attachment to a user even in various environments.

The dry adhesive agent 410 included in the adhesive portion 400 may include a hydrocolloid-based adhesive agent. The hydrocolloid-based adhesive agent may have a characteristic in which reactivity with moisture is less than that of the general acrylic-based adhesive agent, and an adhesion force is again restored in response to the moisture being eliminated. Accordingly, the adhesive portion 400 may include the hydrocolloid-based dry adhesive agent 410, to make re-attachment possible. However, the dry adhesive agent 410 may be configured to include at least one of an acrylic basis, a silicon basis, a rubber basis (natural/synthetic), a urethane basis, and a hydrocolloid basis. The dry adhesive agent 410 may include an adhesive agent that is a combination of the acrylic-based adhesive agent having an excellent initial adhesion force for attachment easiness and the hydrocolloid-based adhesive agent for re-attachment provision.

The wet adhesive agent 420 included in the adhesive portion 400 may include a dopamine-based adhesive agent. The dopamine-based adhesive agent may have a characteristic of having no adhesiveness in a dry environment, but exhibiting an adhesion force upon reaction with moisture. Also, the dopamine-based adhesive agent may have a high stability with the skin.

The adhesive portion 400 may include the dry adhesive agent 410 and the wet adhesive agent 420, which are alternately arranged in a region with the exception of a region 430 in which an electrolyte preservation portion (e.g., the electrolyte preservation portion 352 of FIG. 3C) coupled with an electrode is exposed. The dry adhesive agent 410 and the wet adhesive agent 420 may be alternately arranged to surround each mutually in a ring shape of a different radius. The dry adhesive agent 410 and the wet adhesive agent 420 may have an arbitrary proper area ratio according to a use environment. In response to frequent use in a dry environment being expected, the dry adhesive agent 410 may be configured to have a larger area than the wet adhesive agent 420. In response to frequent use in a wet environment being expected, the wet adhesive agent 420 may be configured to have a larger area than the dry adhesive agent 410. Areas of the dry adhesive agent 410 and the wet adhesive agent 420 may be adjusted according to respective widths (d1 and d2). To guarantee a reliability of an adhesion ability in the wet environment, the width (d2) of the wet adhesive agent 420 may be approximately minimally 3 millimeter (mm) or more.

The dry adhesive agent 410 or the wet adhesive agent 420 may add a process for increasing a surface area for adhesion force improvement. This process may include a plasma etching process, a sanding process using a sand paper, or a sand blast process. In response to the surface area of the wet adhesive agent 420 being increased using at least one of the above-mentioned processes, a ratio of the wet adhesive agent 420 may be decreased. The dry adhesive agent 410 and the wet adhesive agent 420 may have a ratio of 9 to 1.

Figure 5:
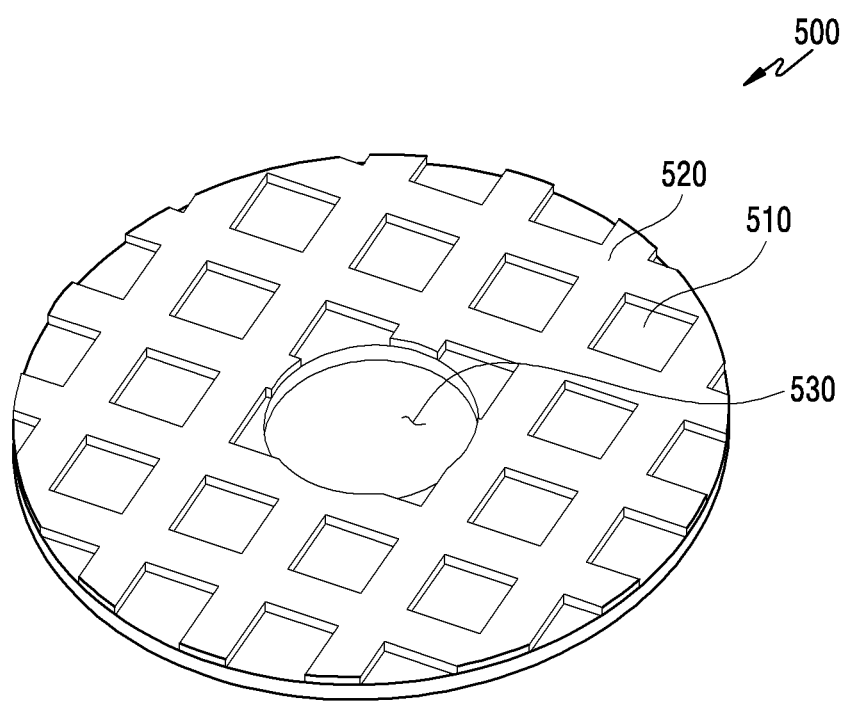
FIG. 5 is a diagram of an adhesive portion, according to an embodiment.

FIG. 5 is a diagram of an adhesive portion 500, according to an embodiment. The adhesive portion 500 explained in FIG. 5 may be a construction which is at least partially similar or the same as the adhesive portion 343 of FIG. 3C.

Referring to FIG. 5, the adhesive portion 500 may include a dry adhesive agent 510 and a wet adhesive agent 520, which are alternately arranged in a lattice form (or network form) in a region with the exception of a region 530 in which an electrolyte preservation portion (e.g., the electrolyte preservation portion 352 of FIG. 3C) coupled with an electrode is exposed. By the adjustment of a gap of lattices and/or a thickness of a line constructing the lattice, the adjustment of a ratio of the dry adhesive agent 510 to the wet adhesive agent 520 may be possible. Other adhesive agents 500 may have arbitrary proper arrangement, form and shape capable of uniformly disposing the dry adhesive agent 510 and the wet adhesive agent 520 at a specific ratio.

Figure 6:
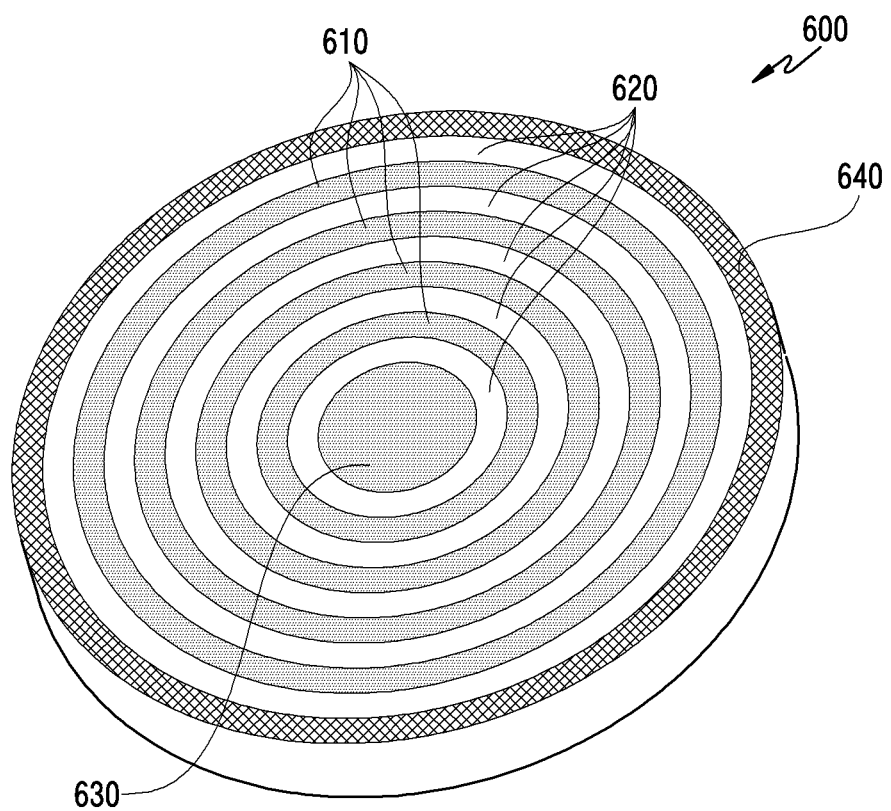
FIG. 6 is a diagram of an adhesive portion, according to an embodiment.

FIG. 6 is a diagram of an adhesive portion 600, according to an embodiment. The adhesive portion 600 explained in FIG. 6 may be a construction which is at least partially similar or the same as the adhesive portion 343 of FIG. 3C.

Referring to FIG. 6, the adhesive portion 600 may include a dry adhesive agent 610, a wet adhesive agent 620, and a waterproof member 640 disposed at an outermost edge. The dry adhesive agent 610 and the wet adhesive agent 620 may be alternately arranged in a region with the exception of a region 630 in which an electrolyte preservation portion (e.g., the electrolyte preservation portion 352 of FIG. 3C) coupled with an electrode is exposed. In response to the adhesive portion 600 being attached to the user's skin, moisture from the external may be infiltrated into the adhesive portion 600 through a side surface of the adhesive portion 600. The adhesive portion 600 may dispose the waterproof member 640 at the outermost edge, thereby preventing the infiltration of moisture from the external. Accordingly, this may prevent a deterioration of an adhesion ability of the dry adhesive agent 610 included in the adhesive agent 600. The waterproof member 640 may be formed of materials which are based on a moisture-permeable waterproof principle of a micro-porous membrane. The moisture-permeable waterproof principle of the micro-porous membrane may be a principle in which the micro-porous membrane prevents the infiltration of rainwater from the external and scatters an internal steam to the external on the assumption that a size of a water particle of a gas state being about 4 μm and a size of a water particle of a liquid state being about 100 to 3,000 μm are different from each other and the micro-porous membrane has a medium size.

The upper end surface (i.e., an opposite surface getting in contact with the user's body) of the pad structure may be mesh-water-repellent coated. After a mesh is used in the upper end surface of the pad structure, the mesh may be water-repellent coated. The mesh-water-repellent coated upper end surface of the pad structure may promote ventilation through a micro hole, but may prevent the moisture infiltration. The pad structure having the mesh-water-repellent coated upper end surface may relatively decrease a ratio of the wet adhesive agent.

Figure 7:
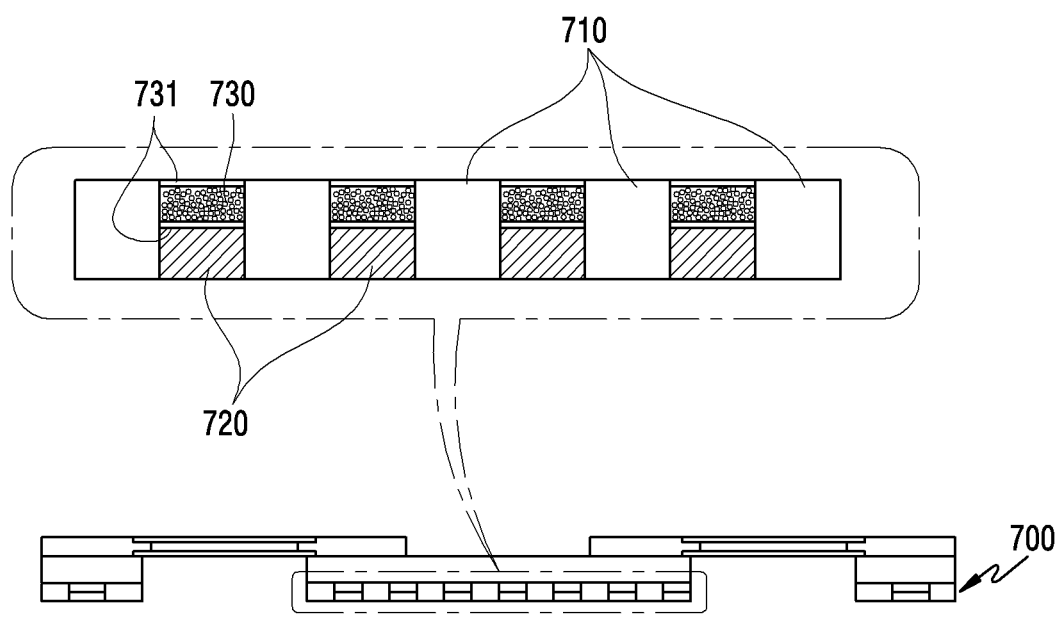
FIG. 7 is a diagram of a cross section of an adhesive portion, according to an embodiment.

FIG. 7 is a diagram of a cross section of an adhesive portion 700, according to an embodiment. The adhesive portion 700 explained in FIG. 7 may be a construction that is at least partially similar or the same as the adhesive portion 343 of FIG. 3C.

Referring to FIG. 7, the adhesive portion 700 may include a wet adhesive agent 710 and a dry adhesive agent 720 alternately arranged, and a dehumidifying agent 730. In response to moisture being infiltrated into the dry adhesive agent 720, the dry adhesive agent 720 may be decreased in its adhesion force and in response to the infiltrated moisture being eliminated (or dried) from the dry adhesive agent 720, the dry adhesive agent 720 may be restored to the original in its adhesion force. The dehumidifying agent 730 may be disposed to be laminated on the dry adhesive agent 720 and may dehumidify the moisture infiltrated into the dry adhesive agent 720. The dehumidifying agent 730 may contribute to keeping and restoring the adhesion force of the dry adhesive agent 720.

The dehumidifying agent 730 may include zeolite. Referring to Chemical Formula 1 below, in response to the zeolite meeting with sweat provided from the user's skin, a hydrogen ion within the zeolite is ion exchanged with a sodium ion included in the sweat, whereby the zeolite may be again reproduced.

$$H_{12}[Al_{12}Si_{12}O_{48}] \cdot 27H_2O + Na^+ \rightarrow Na_{12}[Al_{12}Si_{12}O_{48}] \cdot 27H_2O + H^+ \quad \text{Chemical Formula 1}$$

Accordingly, the dehumidifying agent 730 including the zeolite may have reproducibility and thus, improve an adhesion sustainability of the adhesive portion 700.

The dehumidifying agent 730 may have a powder or fiber form. The dehumidifying agent 730 of the powder or fiber form may be accepted (or supported) in a supporter 731, and be laminated on the dry adhesive agent 720.

Figure 8:
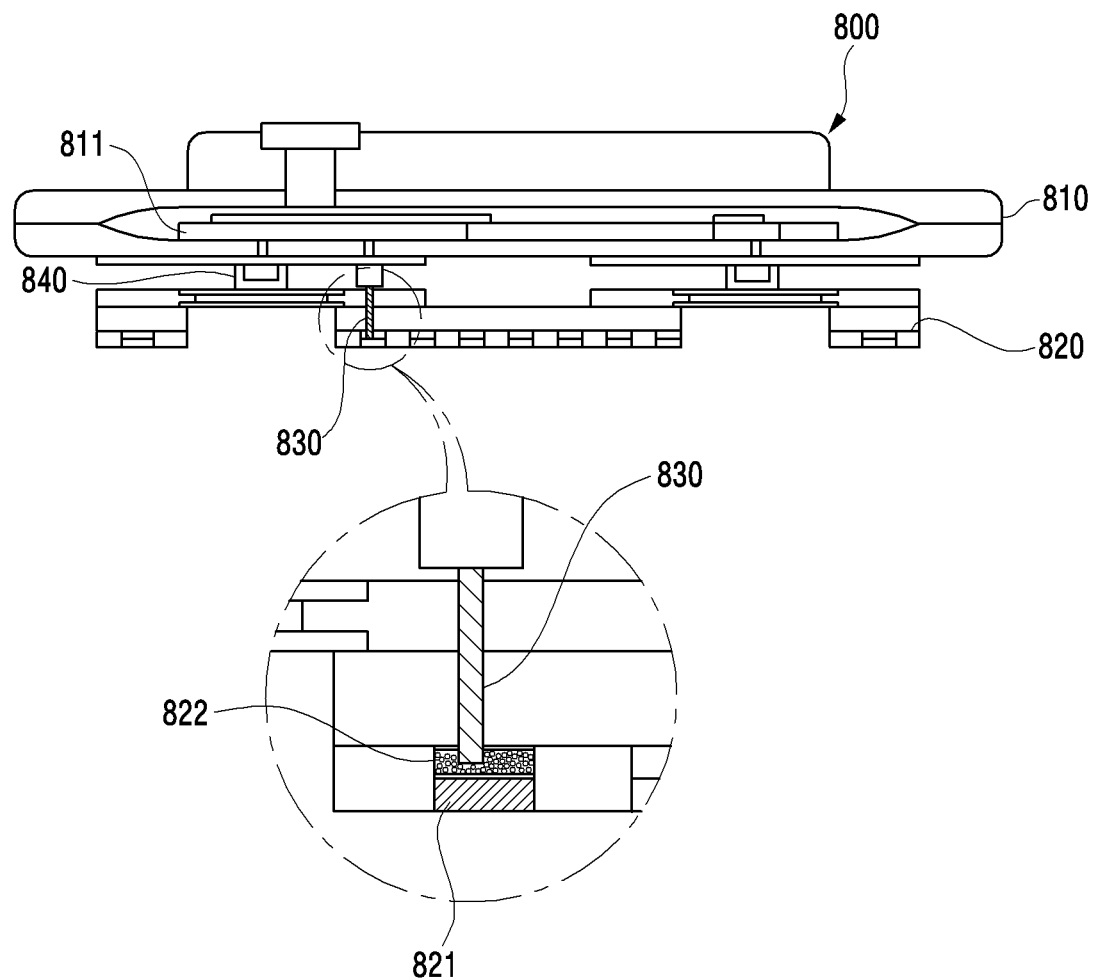
FIG. 8 is a diagram of a cross section of an electronic device including a moisture sensor, according to an embodiment.

FIG. 8 is a diagram of a cross section of an electronic device 800 including a moisture sensor 830, according to an embodiment.

Referring to FIG. 8, the electronic device 800 may include a housing 810, a pad structure 820 coupled to the housing 810, and a moisture sensor 830. The moisture sensor 830 may be configured to obtain a moisture state of a dehumidifying agent 822 disposed on a dry adhesive agent 821 of the pad structure 820. The moisture sensor 830 may have a sensing unit whose one end is positioned in the dehumidifying agent 822. The moisture sensor 830 may be operatively coupled to an electronic component 811 such as a processor (e.g., the processor 320 of FIG. 3B) included in the housing 810. By using the moisture sensor 830, the processor may obtain the moisture state of the dehumidifying agent 822. The moisture state may be identified by measuring an electric conductivity between the moisture sensor 830 and another electrode 840. Accordingly, an adhesion force or life of the dry adhesive agent 821 may be identified. The identifying of an adhesion force or life of the pad structure 820 using the moisture sensor 830 is described in detail through a flowchart of FIG. 9 below.

Figure 9:
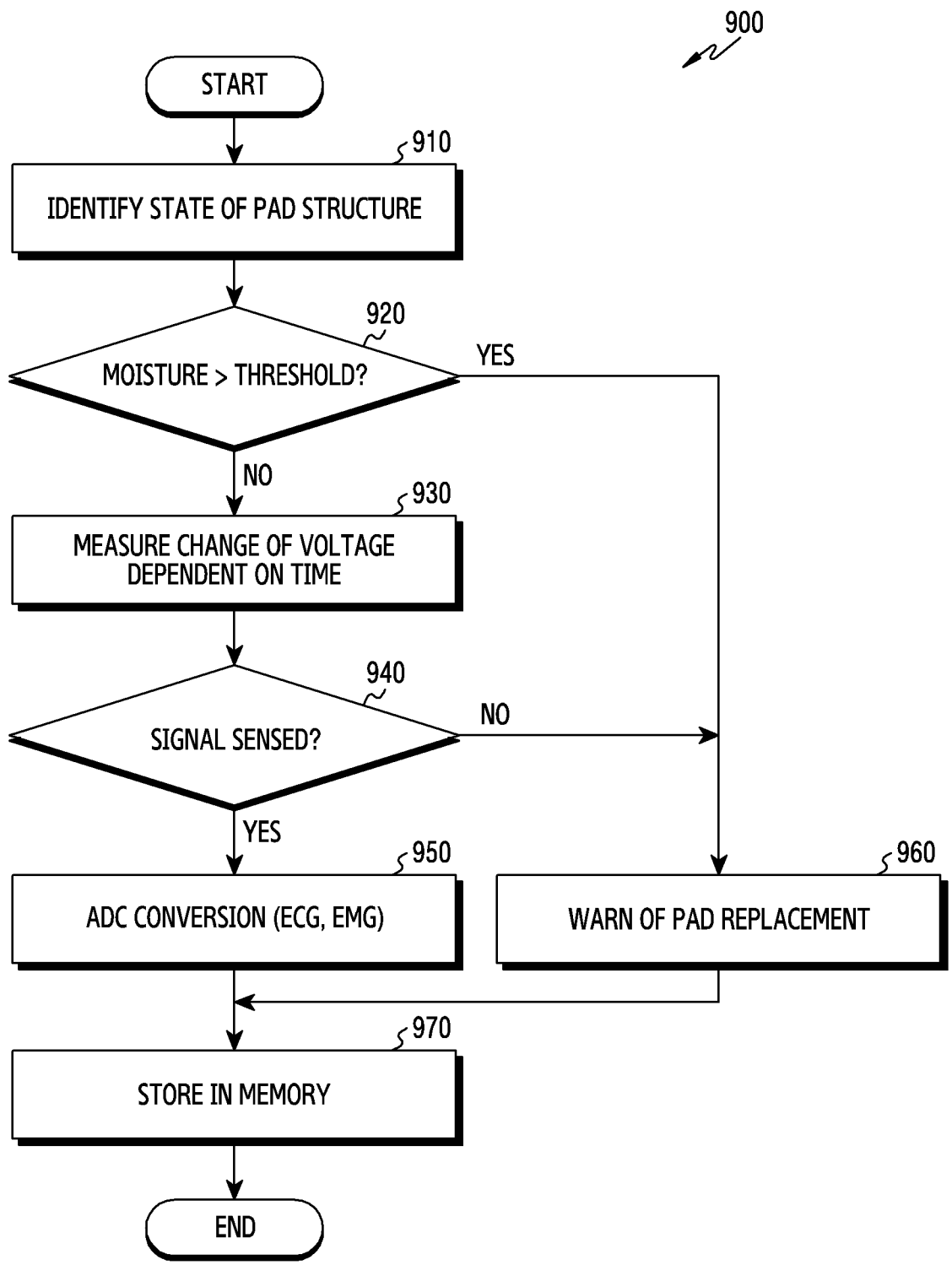
FIG. 9 is a flowchart of a method for identifying an adhesion force or life of a pad structure by using a moisture sensor, according to an embodiment.

FIG. 9 is a flowchart 900 of a method for identifying an adhesion force or life of a pad structure using a moisture sensor, according to an embodiment. The method of FIG. 9 may be carried out by the electronic device 800 explained in FIG. 8, and respective operations (or processes) may be carried out by the processor included in the electronic device 800.

At operation 910, the electronic device 800 may identify a state of the pad structure 820. The identifying of the state of the pad structure 820 may be carried out by a user input for a button (e.g., the button 361 of FIG. 3A) disposed in the electronic device 800. The identifying of the state of the pad structure 820 may be caused by a signal received from another electronic device (e.g., the electronic device 104 of FIG. 1). The electronic device 800 may identify the state of the pad structure 820 every a preset period.

At operation 920, the electronic device 800 may identify whether a moisture state of the dehumidifying agent 822 exceeds a threshold, on the basis of the identified state of the pad structure 820. The electronic device 800 may identify the moisture state of the dehumidifying agent 822 by using the moisture sensor 830.

In response to the identified moisture state exceeding the threshold, at operation 960, the electronic device 800 may notify a warning of replacement of the pad structure 820. In response to the identified moisture state exceeding the threshold, the electronic device 800 may identify that it is a time to replace the pad structure 820, in that there is a great possibility in which the pad structure 820 is unintentionally detached due to a deterioration of an adhesion force of the dry adhesive agent 821. The replacement warning notification may include flickering an indicator (e.g., the indicator 362 of FIG. 3A) according to a specific pattern, or directly displaying this notification on a display (e.g., the display 363 of FIG. 3A). Further, at a time of the warning of replacement of the pad structure 820 at operation 960, information about the time may be stored in a memory and thus be provided to make it possible to be identified outside. The electronic device 800 may transmit the warning of replacement of the pad structure 820 to an external device through a communication module (e.g., the communication module 190 or the communication module 313).

In response to the identified moisture state being equal to or being less than the threshold, at operation 930, the electronic device 800 may measure a change of a voltage dependent on a time from the pad structure 820.

At operation 940, the electronic device 800 may identify whether a signal is sensed from the pad structure 820. The electronic device 800 may identify whether a signal is sensed from the pad structure 820 depending on whether the voltage change is measured from the pad structure 820. In response to it being identified that the signal is not sensed from the pad structure 820, it means that the pad structure 820 is unintentionally detached from the user's skin and therefore, at operation 960, the electronic device 800 may notify a warning of replacement of the pad structure 820. The electronic device 800 may set a reference voltage for signal sensing. In response to the voltage measured at operation 930 being equal to or being less than the reference voltage, the electronic device 800 may regard that the pad structure 820 is unintentionally detached (lead-off) from the skin. The electronic device 800 may apply a reference current (e.g., a few nA of current or less) to the pad structure 820 during a set time (e.g., a few seconds) by periods or upon user request and then, measure resistance. In response to the measured resistance being equal to or being greater than a preset reference resistance (e.g., about 500 MΩ), the electronic device 800 may regard that the pad structure 820 is unintentionally detached (lead-off) from the skin, and warn of the replacement of the pad structure 820.

In response to it being identified that the signal is sensed from the pad structure 820, at operation 950, the electronic device 800 may convert the measured voltage by an analog-to-digital converter (ADC), and provide biometric information (e.g., ECG data and/or electromyogram (EMG) data).

At operation 970, the electronic device 800 may store the provided biometric information in the memory. The biometric information stored in the memory may be displayed on a display (e.g., the display 363 of FIG. 3A), or be transmitted to another electronic device (e.g., the electronic device 104 of FIG. 1) or server (e.g., the server 108 of FIG. 1) wiredly/wirelessly coupled with the electronic device 800.

Figure 10:
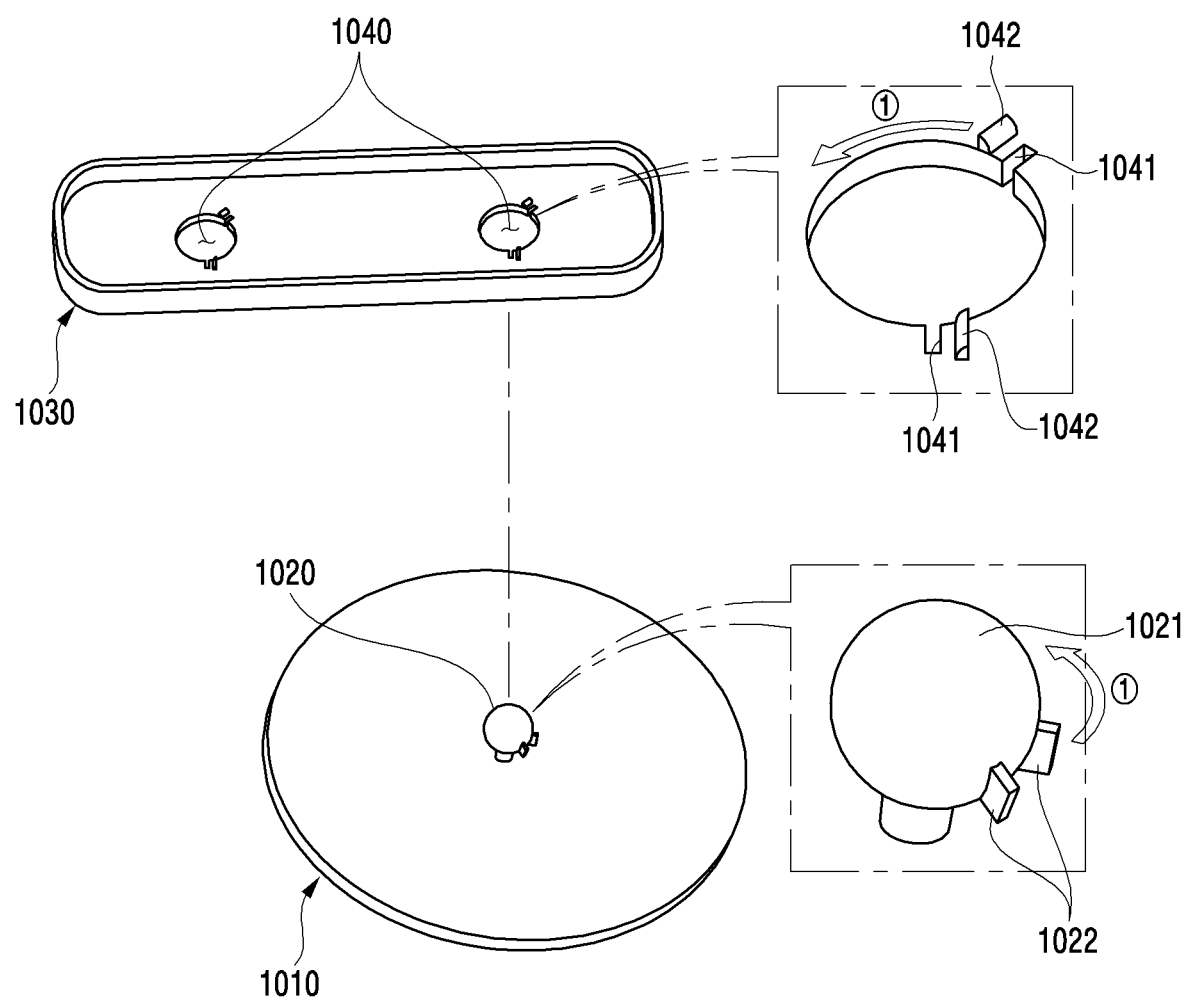
FIG. 10 is a diagram of a coupling structure of a pad structure and a housing, according to an embodiment.

FIG. 10 is a diagram of a coupling structure of a pad structure 1010 and a housing 1030, according to an embodiment. The pad structure 1010 and the housing 1030 explained in FIG. 10 may be at least similar or the same as the housing 310 and the pad structure 320 of FIG. 3B.

Referring to FIG. 10, the pad structure 1010 may include a coupling portion 1020 coupled (combined) to the housing 1030. The coupling portion 1020 may have an electrode 1021 (e.g., the first electrode 331 or second electrode 332 of FIG. 3B) of a substantially circular shape. The electrode 1021 may be formed of a conductive material (e.g., metal), or be formed by coating a nonconductive material with a conductive polymer or a conductive material.

The electrode 1021 may be electrically coupled with a printed circuit board (e.g., the printed circuit board 312 of FIG. 3B). The electrode 1021 may include at least one protrusion portion 1022 which protrudes in a direction substantially vertical to a direction of being inserted. The housing 1030 may further include an opening 1040 and a cut portion 1041. The opening 1040 may be of a shape corresponding to the electrode 1021, wherein the electrode 1021 may be inserted into the opening 1040. The protrusion portion 1022 may be inserted into the cut portion 1041.

The housing 1030 may further include a locking jaw 1042 around the opening 1040. The locking jaw 1042 may be slanted at its one surface with respect to a bottom surface of the housing 1030 wherein the protrusion portion 1022 may pass through the cut portion 1041 and then rotate in an arrow direction, and may meet at right angles at its other surface with the bottom surface of the housing 1030.

In response to being rotated in the arrow direction, at least one protrusion portion 1022 of the pad structure 1010 is caught by the bottom surface of the housing 1030, and is limited in its movement to a position of the cut portion 1041 by means of the right-angled surface of the locking jaw 1042, so a separation of the pad structure 1010 from the housing 1030 may be confined.

The pad structure 1010 may be free to perform a motion such as inclination, rotation, etc., with respect to the housing 1030. Accordingly, the pad structure 1010 may move adaptively to deformation such as expansion, contraction, etc., of the user's skin to which the pad structure 1010 is attached. This may result in the improvement of attachment sustainability of the pad structure 1010 and a decrease of a pain of the user's skin.

According to an embodiment, an electronic device (e.g., an electronic device (101), an electronic device (300), an electronic device (800)) may include a housing (e.g., a housing (310), a housing (810), a housing (1030)) including a first housing surface facing a first direction, at least one electronic component (e.g., an electronic component (811)) positioned within the housing, at least one electrode exposed through the first housing surface and electrically coupled with the electronic component, and a pad structure (e.g., a pad structure (320), a pad structure (820), a pad structure (1010)) coupled with the housing. The pad structure includes a first adhesive layer (e.g., a pad upper end portion (342)) which includes a first adhesive surface attached to at least a part of the first housing surface and a second adhesive surface of an opposite direction to the first adhesive surface, a second adhesive layer (e.g., an adhesive portion (343)) which includes a third adhesive surface facing the second adhesive surface, and a fourth adhesive surface of an opposite direction to the third adhesive surface. The second adhesive layer includes at least one first region which includes a first adhesive material (e.g., a dry adhesive agent (410), a dry adhesive agent (510), a dry adhesive agent (610), a dry adhesive agent (720), a dry adhesive agent (821)) having a first adhesive strength in response to water or humidity existing and having a second adhesive strength greater than the first adhesive strength in response to the water or humidity not existing, and at least one second region which abuts the first region and includes a second adhesive material (e.g., a wet adhesive agent (420), a wet adhesive agent (520), a wet adhesive agent (620), a wet adhesive agent (710)) having a third adhesive strength in response to the water or humidity not existing, and having a fourth adhesive strength greater than the third adhesive strength in response to the water or humidity existing. The pad structure includes a substrate layer (e.g., an adhesive fixing film portion (341)) in contact with the first adhesive layer and the second adhesive layer, and positioned therebetween, at least one opening (e.g., an opening (360)) formed through at least a part of the pad structure, and an electrolyte (e.g., an electrolyte (351)) in contact with the at least one electrode and filling at least part of the opening.

The first adhesive material may include at least one of acrylic-based, silicon-based, rubber-based, urethane-based, and/or hydro-colloid-based adhesive agents.

The second adhesive material may include a polydopamine-based adhesive agent.

The first region may include a lattice structure which defines a plurality of openings forming the at least one second region.

The at least one first region may include a plurality of first regions, and the at least one second region may include a plurality of second regions forming a repeated pattern with the plurality of first regions.

The electronic component may include an electronic circuit providing ECG data.

The pad structure may further include a layer or sheet attached to the fourth adhesive surface.

The layer or sheet may include polyethylene terephthalate (PET).

The pad structure may further include a water proof member (e.g., a water proof member (640)) disposed to surround a side surface of the pad structure at an outermost edge.

A dehumidifying agent (e.g., a dehumidifying agent (730), a dehumidifying agent (822)) may be further disposed on the first region.

The dehumidifying agent includes zeolite including a hydrogen ion therein and reproduced by a sodium ion.

The electronic device may further include a moisture sensor (e.g., a moisture sensor (830)) configured to identify a moisture state of the dehumidifying agent.

The moisture sensor is configured to recognize the moisture state of the dehumidifying agent by obtaining an electric conductivity between the moisture sensor and the electrode.

The electronic component may include at least one processor (e.g., a processor (120), a processor (311), a processor (320)). The processor is configured to provide a warning notification of notifying the replacement of the pad structure in response to the moisture state measured through the moisture sensor exceeding a threshold.

The pad replacement warning notification is provided through an indicator (e.g., an indicator (362)) or display (e.g., a display (363)) included in the electronic device.

The pad structure substantially has a circular shape and further includes at least one other electrode (e.g., an electrode (1021)) protruding from the pad structure. The housing comprises an opening (e.g., an opening (1040)) into which the protruding other electrode is insertable.

The protruding other electrode may include a protrusion portion (e.g., a protrusion portion (1022)) which protrudes in a direction substantially vertical to a direction of being inserted into the opening, and the opening may further include a cut portion (e.g., a cut portion (1041)) for inserting the protrusion portion therein.

The housing may further include a locking jaw (e.g., a locking jaw (1042)) configured to enable the protrusion portion to be caught by an edge of the opening.

According to an embodiment, an electronic device (e.g., an electronic device (101), an electronic device (300), an electronic device (800)) may include a housing (e.g., a housing (310), a housing (810), a housing (1030)) including at least one electronic component (e.g., an electronic component (811)), and a pad structure (e.g., a pad structure (320), a pad structure (820), a pad structure (1010)) coupled with the housing, and attached to a user's body. The pad structure includes a first adhesive material (e.g., a dry adhesive agent (410), a dry adhesive agent (510), a dry adhesive agent (610), a dry adhesive agent (720), a dry adhesive agent (821)) having an adhesive strength at which the electronic device holds attachment in response to water or humidity not existing, and a second adhesive material (e.g., a wet adhesive agent (420), a wet adhesive agent (520), a wet adhesive agent (620), a wet adhesive agent (710)) abutting the first adhesive material and having an adhesive strength at which the electronic device holds the attachment in response to the water or humidity existing.

The pad structure may further include a dehumidifying agent (e.g., a dehumidifying agent (730), a dehumidifying agent (822)) disposed on the first adhesive material.

The electronic device may guarantee a sustainability of attachment, and make possible re-attachment, and prevent a user's inconvenience and/or skin trouble, etc. (i.e., biocompatibility is excellent). The electronic device may notify a user of a time of replacement of the pad structure attached to the user's body. Other various effects may be provided.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

What is claimed is:

1. An electronic device comprising:
  a housing including a first housing surface facing a first direction;
  at least one electronic component positioned within the housing;
  at least one electrode exposed through the first housing surface and electrically coupled with the electronic component; and
  a pad structure coupled with the housing,
  wherein the pad structure comprises:
    a first adhesive layer which includes a first adhesive surface attached to at least a part of the first housing surface and a second adhesive surface of an opposite direction to the first adhesive surface;
    a second adhesive layer which includes a third adhesive surface facing the second adhesive surface, and a fourth adhesive surface of an opposite direction to the third adhesive surface, the second adhesive layer comprising:
      at least one first region which includes a first adhesive material having a first adhesive strength in response to existing water or humidity, and having a second adhesive strength greater than the first adhesive strength in response to the lack of existing water or humidity, and
      at least one second region which abuts the at least one first region, which includes a second adhesive material having a third adhesive strength in response to the lack of existing water or humidity, and having a fourth adhesive strength greater than the third adhesive strength in response to existing water or humidity;

a substrate layer in contact with the first adhesive layer and the second adhesive layer, and positioned therebetween;

at least one opening formed through at least a part of the pad structure; and an electrolyte preservation portion in contact with the at least one electrode and filled with an electrolyte, wherein the electrolyte preservation portion is included in the first adhesive layer, exposed to outside through the at least one opening to attach to a user's body, and distinguished from the at least one first region and the at least one second region.

2. The electronic device of claim 1, wherein the first adhesive material comprises at least one of acrylic-based, silicon-based, rubber-based, urethane-based, and/or hydrocolloid-based adhesive agents.

3. The electronic device of claim 2, wherein the second adhesive material comprises a polydopamine-based adhesive agent.

4. The electronic device of claim 1, wherein the adhesive strength of the first adhesive material varies in response to existing water or humidity, and the adhesive strength of the second adhesive material varies in response to a lack of existing water or humidity.

5. The electronic device of claim 1, wherein the at least one first region comprises a plurality of first regions, and the at least one second region comprises a plurality of second regions forming a repeated pattern with the plurality of first regions.

6. The electronic device of claim 1, wherein the electronic component comprises an electronic circuit providing electrocardiogram (ECG) data.

7. The electronic device of claim 1, wherein the pad structure further comprises a layer or sheet attached to the fourth adhesive surface.

8. The electronic device of claim 7, wherein the layer or sheet comprises polyethylene terephthalate (PET).

9. The electronic device of claim 1, wherein the pad structure further comprises a water proof member disposed to surround a side surface of the pad structure at an outermost edge.

10. The electronic device of claim 1, wherein a dehumidifying agent is further disposed on the at least one first region.

11. The electronic device of claim 10, wherein the dehumidifying agent comprises zeolite comprising a hydrogen ion therein and is reproduced by a sodium ion.

12. The electronic device of claim 10, further comprising a moisture sensor configured to identify a moisture state of the dehumidifying agent.

13. The electronic device of claim 12, wherein the moisture sensor is configured to recognize the moisture state of the dehumidifying agent by obtaining an electric conductivity between the moisture sensor and the at least one electrode.

14. The electronic device of claim 12, wherein the electronic component comprises at least one processor, and the processor is configured to provide a warning notification notifying a replacement of the at least a part of the pad structure in response to the moisture state measured through the moisture sensor exceeding a threshold.

15. The electronic device of claim 14, wherein the warning notification is provided through an indicator or display included in the electronic device.

16. The electronic device of claim 1, wherein the pad structure has a substantially circular shape and further comprises at least one other electrode protruding from the pad structure, and the housing includes an opening into which the protruding other electrode is insertable.

17. The electronic device of claim 16, wherein the protruding other electrode comprises a protrusion portion which protrudes in a direction substantially vertical to a direction of being inserted into the opening, and the opening further comprises a cut portion for inserting the protrusion portion therein.

18. The electronic device of claim 17, wherein the housing further includes a locking jaw configured to enable the protrusion portion to be caught by an edge of the opening.

19. The electronic device of claim 1, wherein the at least one first region and the at least one second region are concentrically arranged around the least one opening.

* * * * *